(12) United States Patent
Jacobson

(10) Patent No.: US 9,408,740 B2
(45) Date of Patent: Aug. 9, 2016

(54) NECK PAIN RELIEVING DEVICES

(71) Applicant: Mayo Foundation for Medical Education and Research, Rochester, MN (US)

(72) Inventor: Mark A. Jacobson, Grand Meadow, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 292 days.

(21) Appl. No.: 13/953,957

(22) Filed: Jul. 30, 2013

(65) Prior Publication Data

US 2014/0026894 A1  Jan. 30, 2014

Related U.S. Application Data

(60) Provisional application No. 61/677,345, filed on Jul. 30, 2012.

(51) Int. Cl.
*A61G 15/00* (2006.01)
*A61F 5/37* (2006.01)
*A61F 5/01* (2006.01)

(52) U.S. Cl.
CPC .............. *A61F 5/3707* (2013.01); *A61F 5/01* (2013.01)

(58) Field of Classification Search
CPC ... G10L 17/26; A45B 1/04; A45F 2200/0566; A61F 5/01; A61F 5/3707; A61F 5/055; A61F 5/024; A61F 2250/0004; A61F 2250/0065; H04M 1/271; H04M 1/72561; H04M 2201/40; H04M 2201/54; H04M 2201/60; H04M 2203/2061; H04M 3/382; H04M 3/493; H04M 3/53; A47C 7/383; Y10S 128/23; A63B 21/05; A63B 2208/12; A63B 23/025; A63B 23/03; A63B 2022/206; A63B 21/0085; A63B 21/02; A63B 21/068; A63B 2208/0219; A63B 22/205; A63B 23/0211; A63B 23/0216; A63B 21/0611; A63B 2225/093; A63B 21/06; A63B 21/0615; A63B 2210/50; B60N 2/005; B60N 2/01; B60N 2/265

USPC ............................... 602/17–19; 128/857, 870
See application file for complete search history.

(56) References Cited

U.S. PATENT DOCUMENTS 5,495,867 A * 3/1996 Block .............................. 135/65
8,684,957 B2 * 4/2014 Bonutti ........................... 602/19

* cited by examiner

*Primary Examiner* — Michael Brown
(74) *Attorney, Agent, or Firm* — Fish & Richardson P.C.

(57) ABSTRACT

This document provides methods and materials related to relieving neck pain. For example, neck pain relieving devices as well as methods for making and using neck pain relieving devices to provide relief from chronic or acute neck pain by providing support to the back of the head are provided.

20 Claims, 5 Drawing Sheets

NECK PAIN RELIEVING DEVICES

CROSS REFERENCE TO RELATED APPLICATIONS

This application claims the benefit of U.S. Provisional Application Ser. No. 61/677,345, Jul. 30, 2012. The disclosure of the prior application is considered part of (and is incorporated by reference in) the disclosure of this application.

BACKGROUND

1. Technical Field

This document relates to methods and materials for relieving neck pain. For example, this document relates to neck pain relieving devices and methods for making and using neck pain relieving devices configured to provide relief from chronic or acute neck pain by providing support to the back of the head.

2. Background Information

Neck pain is a very common problem that can affect anyone. While the number of people suffering from neck pain is not known, the number is estimated to be in the tens of millions. Neck pain can be caused by many different events, for example, a traumatic injury, illness, tension, stress and muscular strain. The pain can be acute, chronic, or recurrent. Some people are not able to work, go to school, enjoy a social life, participate in sports, or travel due to neck pain. Some can become depressed and develop social, marital, and family problems.

SUMMARY

This document provides methods and materials related to relieving neck pain. For example, this document provides neck pain relieving devices and methods for making and using neck pain relieving devices configured to provide relief from chronic or acute neck pain by providing support to the back of the head. As described herein, neck pain relieving devices can be designed such that they support a least a portion of the weight of the head, thereby unloading at least some pressure from the cervical spine and cervical muscles. In some cases, a neck pain relieving device provided herein can include a rod with a first and second end, a head support component, and a chest pivot component. The head support component can attach to the second end of the rod. The chest pivot component can attach to the rod between the first and second end. The first end of the rod can be designed for a user to hold the neck pain relieving device. The neck pain relieving device can work as a type I lever. Effort can be applied at the first end of the rod by a user. The chest pivot component can be a fulcrum. The head support component can push against the back of the head, exerting a larger force over a small distance than the force exerted at the first end of the rod. As described herein, neck pain relieving devices can be designed such that they are ambulatory. Having the ability to relieve neck pain with a neck pain relieving device that can be used anywhere can help neck pain sufferers regain a normal, more comfortable life.

In general, one aspect of this document features a device for relieving neck pain. The device comprises, or consists essentially of, (a) a rod element having a first end region, a second end region, and a longitudinal axis, (b) a head support component having a longitudinal axis and extending from the second end region of the rod element, and (c) a chest pivot component having a longitudinal axis and extending from a position of the rod element located between the first end region and the second end region, wherein the longitudinal axis of the head support component and the longitudinal axis of the chest pivot component are substantially perpendicular to the longitudinal axis of the rod element, wherein the longitudinal axis of the head support component and the longitudinal axis of the chest pivot component are substantially parallel, and wherein the head support component is positioned to contact the back of a head of a human user when the chest pivot component is positioned in contact with the upper chest of the human user. The head support component can be covered by a cushion. The cushion can comprise material selected from the group consisting of gel, micro beads, visco-elastic polyurethane foam, foam rubber, buckwheat, cotton, and combinations thereof. The head support component and the cushion can be covered with a soft sleeve configured to fit over the head support component and the cushion, wherein the soft sleeve can define one open end and comprises at least one fastener configured to hold the open end closed. The soft sleeve can define an open slit along at least a portion of the length of the soft sleeve and comprises at least one fastener configured to hold the two sides of the slit together. The soft sleeve can comprise material selected from the group consisting of cotton, leather, suede, polyester, acrylic, felt, vinyl, and combinations thereof. The fastener can be selected from the group consisting of hook and loop closures, at least two magnets, snaps, buttons, ties, zippers, and combinations thereof. The chest pivot component can be covered by a cushion. The cushion can comprise material selected from the group consisting of gel, micro beads, visco-elastic polyurethane foam, foam rubber, buckwheat, cotton, memory foam, and combinations thereof. The chest pivot component and the cushion can be covered with a soft sleeve configured to fit over the chest pivot component and the cushion, wherein the soft sleeve can define an open end and can comprise at least one fastener configured to hold the open end closed. The soft sleeve can define an open slit along at least a portion of the length of the soft sleeve and can comprise at least one fastener configured to hold the two sides of the slit together. The soft sleeve can comprise material selected from the group consisting of cotton, leather, suede, polyester, acrylic, felt, vinyl, and combinations thereof. The fastener can be selected from the group consisting of hook and loop closures, at least two magnets, snaps, buttons, ties, zippers, and combinations thereof. The head support component can be configured to support at least a portion of the weight of the head. The head support component can be rectangular. The head support component can comprise material selected from the group consisting of stainless steel, aluminum, hard plastic, wood, and combinations thereof. The rod element between the chest pivot component and the head support component can be configured to be telescoping to adjust the length of the rod element. The chest pivot component can be moveable along the longitudinal axis of the rod element. The chest pivot component can be configured to pivot between the first end region and the second end region of the rod element. The chest pivot component can be cylindrical. The chest pivot component can comprise material selected from the group consisting of stainless steel, aluminum, hard plastic, wood, and combinations thereof. The rod element can be straight. The rod element at the second end region can angle between about 5 and about 30 degrees from the longitudinal axis of the rod element, wherein the second end region of the rod element can angle towards a line that is 180 degrees from the longitudinal axis of the chest pivot component. The second end region of the rod element can turn towards the longitudinal axis of the rod element at the level of the head support component. The head support component can be configured to fit over an end of the second end region of the rod element. The rod element can be cylindrical. The rod element can be configured to fit users of various sizes. The rod element between the first end region of the rod element and the chest pivot component can be telescoping to have an adjustable length. The first end region of the rod element can define grooves or indentations. The first end region of the rod element can be covered with a non-slip material. The non-slip material can be selected from the group consisting of, rubber, PVC-coated fabric, polychloroprene, silicone, latex, molded plastic, and combinations thereof. The rod element comprises material selected from the group consisting of stainless steel, aluminum, hard plastic, wood, and combinations thereof. The head support component and the chest pivot component can be attached to the rod element with a hinge such that the head support component and the chest pivot component fold flat along the length of the rod element.

In another aspect, this document features a method of relieving neck pain. The method comprises, or consists essentially of, supporting the back of the head of a human user with a device set forth herein.

In another aspect, this document features a method of facilitating balance of a human user. The method comprises, or consists essentially of, placing weight of the human user on a device set forth herein to support balance of the human user while the human user is standing, stepping, walking, or climbing.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

This document provides methods and materials related to relieving neck pain. For example, this document provides neck pain relieving devices and methods for making and using neck pain relieving devices configured to provide relief from chronic or acute neck pain by providing support to the back of the head. A neck pain relieving device provided herein can include a rod, a head support component, and a chest pivot component. The neck pain relieving device can be configured such that it makes a type I lever with the chest pivot component acting as a fulcrum. With the back of the head in contact with the head support component at one end of the rod, force can be applied at the other end of the rod to cause the head support component to push against the back of the head. The support of the head provided by the type I lever can relieve at least a portion of the load on the cervical spine and the cervical muscles, resulting in neck pain relief.

Figure 1:
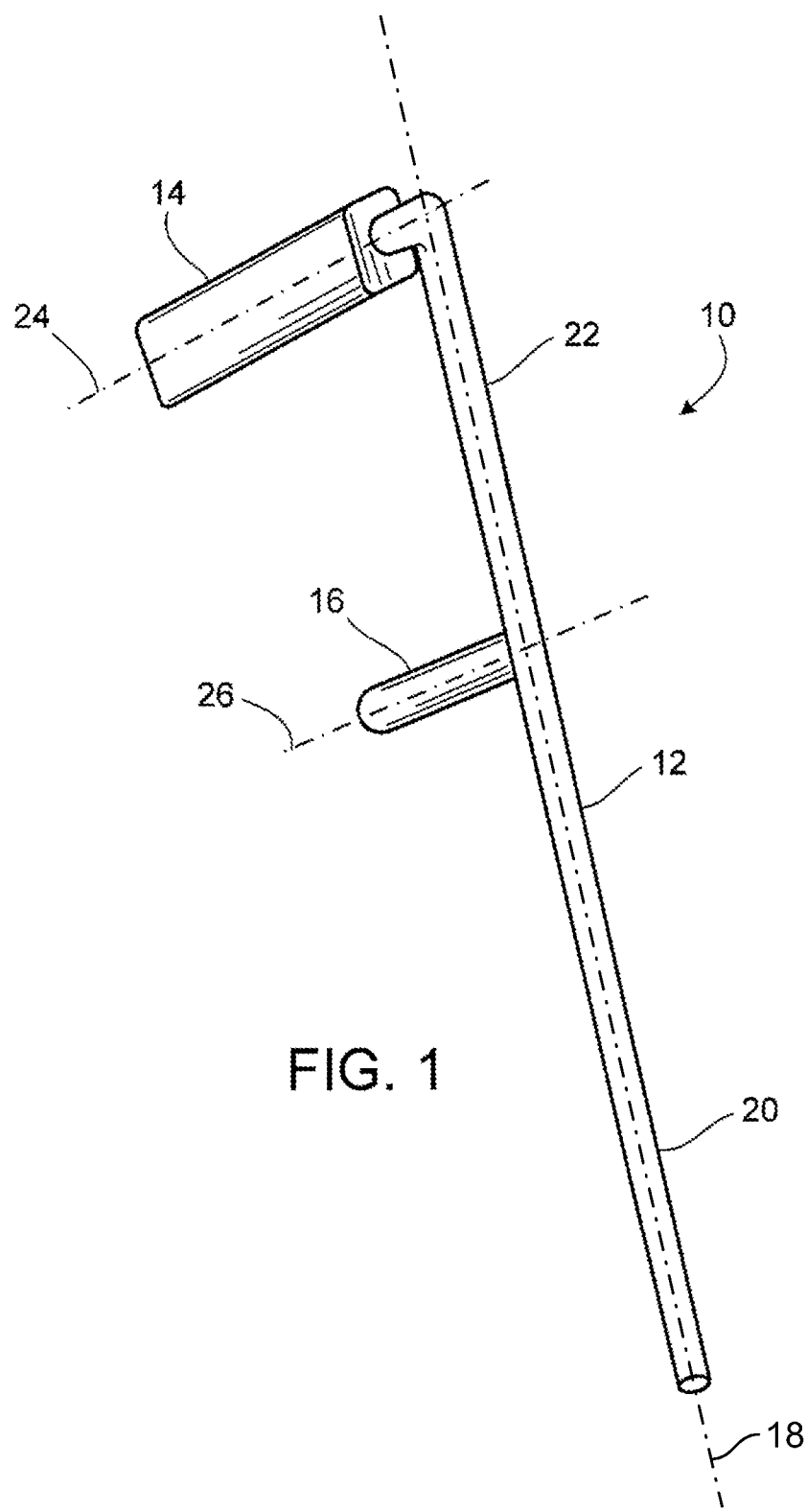
FIG. 1 is a perspective view of an exemplary neck pain relieving device provided herein.

With reference to FIG. 1, neck pain relieving device 10 can include a rod element 12, a head support component 14, and a chest pivot component 16. Rod element 12 can be configured to have a longitudinal axis 18 with first end 20 and second end 22. First end 20 of rod element 12 can be configured for a user to hold neck pain relieving device 10. Head support component 14 can be configured to have a longitudinal axis 24 and to be integral with or to be attached to second end 22 of rod element 12. Longitudinal axis 24 of head support component 14 can be perpendicular or substantially perpendicular to longitudinal axis 18 of rod element 12. Chest pivot component 16 can be configured to have a longitudinal axis 26 and to be integral with or to be attached to rod element 12 between first end 20 and second end 22. Longitudinal axis 26 of chest pivot component 16 can be perpendicular or substantially perpendicular to longitudinal axis 18 of rod element 12. Longitudinal axis 24 of head support component 14 and longitudinal axis 26 of chest pivot component 16 can be parallel or substantially parallel to one another and extend in the same direction or a substantially same direction from longitudinal axis 18 of rod element 12. For example, with reference to FIG. 2, when neck pain relieving device 10 is in use, rod element 12 can extend up and past the shoulder such that head support component 14 rests against the back of the head and chest pivot component 16 rests against the upper chest. In some cases, a neck pain relieving device provided herein can have (a) two head support components and one chest pivot component, (b) one head support component and two chest pivot components, or (c) two head support components and two chest pivot components.

A head support component, a chest pivot component, or both of a neck pain relieving device provided herein can be covered with a cushion. The presence of a cushion covering a head support component and/or a chest pivot component can provide comfort for the user of a neck pain relieving device. A cushion can provide a soft layer between the back of the user's head and a rigid head support component and between the user's upper chest and a rigid chest pivot component. The cushion can be configured to have a central lumen with a shape and dimensions that allow the cushion to fit over a head support component or a chest pivot component. The thickness of the cushion can range between about 2 cm and about 8 cm (e.g., between about 3 cm and about 8 cm, between about 4 cm and about 8 cm, between about 5 cm and about 8 cm, between about 2 cm and about 7 cm, between about 2 cm and about 6 cm, or between about 4 cm and about 5 cm). Examples of materials that can be used to make a cushion provided herein include, without limitation, gel, micro beads, visco-elastic polyurethane foam, foam rubber, buckwheat, memory foam, and cotton.

Figure 3A:
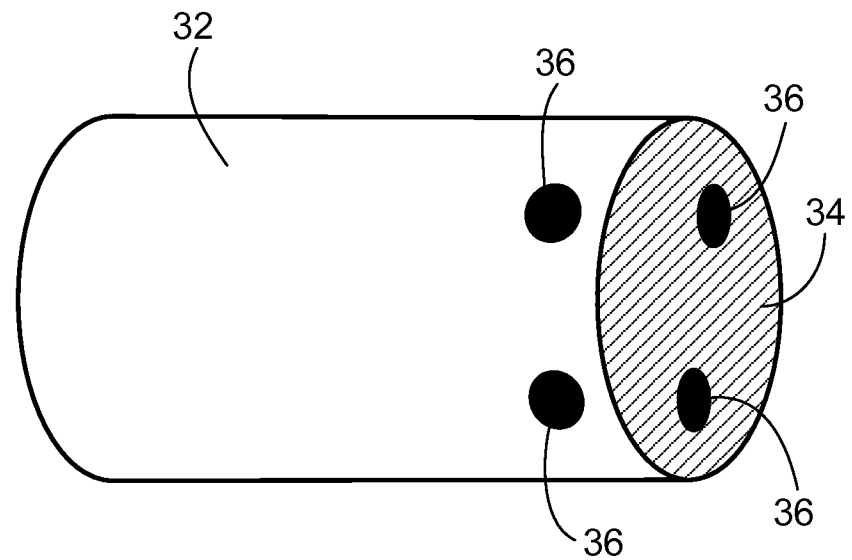
FIG. 3A is a side view of an exemplary soft sleeve provided herein.
Figure 3B:
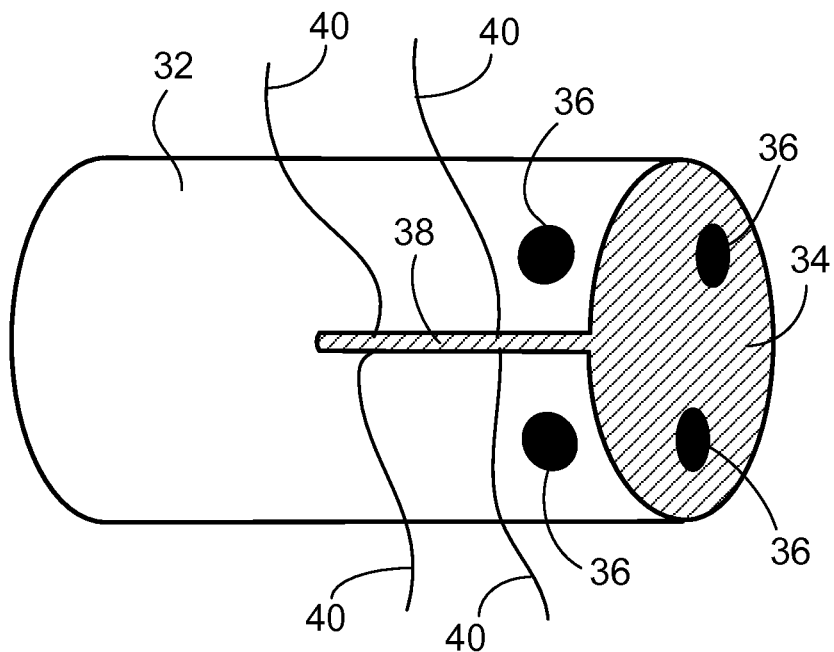
FIG. 3B is a side view of an exemplary soft sleeve provided herein.

In some cases, a cushion covering a head support component and/or a chest pivot component of a neck pain relieving device provided herein can be covered by a soft sleeve. The soft sleeve can be configured to contain the size and the shape of the cushion and head support component or cushion and chest pivot component. For example, as shown in FIG. 3A, soft sleeve 32 can have a single open end 34 that slides over the cushion and head support component or cushion and chest pivot component. Once soft sleeve 32 is fit over the cushion and head support component or cushion and chest pivot component, it can be secured in place by at least one fastener 36. In some cases, as shown in FIG. 3B, soft sleeve 32 can have a slit 38 along at least a portion of the length of soft sleeve 32 beginning at open end 34. Once soft sleeve 32 is in place over the cushion and head support component or cushion and chest pivot component, it can be secured in place by at least one fastener 36. Examples of fasteners that can be used to secure open end 34 and slit 38 of soft sleeve 32 include, without limitation, hook and loop closures, at least two magnets, snaps, buttons, ties 40, and zippers. Soft sleeve 32 of a neck pain relieving device provided herein can be composed of soft material that can be removed and cleaned. Examples of soft materials that can be used to make soft sleeve 32 include, without limitation, cotton, leather, suede, polyester, acrylic, felt, and vinyl. The soft material used to make soft sleeve 32 can be any color or collection of colors with any pattern or collection of patterns.

A head support component of a neck pain relieving device provided herein can be integral with or attached to a second end of a rod element. The exact position of a head support component can vary at the second end of a rod element. For example, with reference to FIG. 1, head support component 14 can be located at the end of second end 22 of rod element 12. In some cases, head support component 14 can be flush with the end of rod element 12. In some cases, as in FIG. 2, head support component 14 can be located near, but not at the end, of rod element 12. Some of second end 22 of rod element 12 can extend beyond the position of head support component 14.

Figure 2:
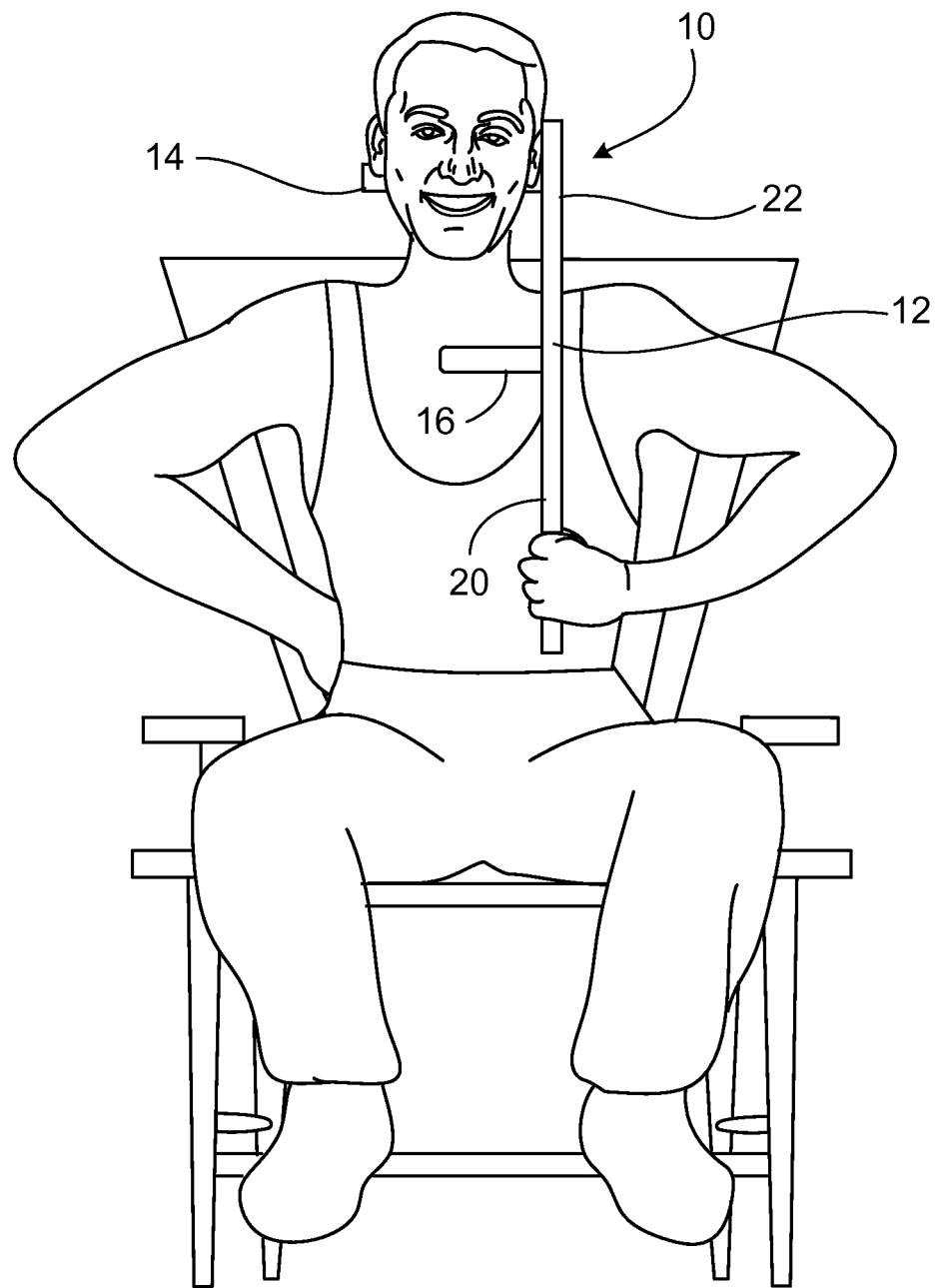
FIG. 2 is a front view of an exemplary neck pain relieving device provided herein while in use.

A head support component of a neck pain relieving device provided herein can have any appropriate configuration that allows a head support component to have at least one surface in contact with the back of the head of a user such that the head support component can support at least some of the weight of the user's head. For example, as shown in FIG. 2, head support component 14 can be rectangular. Head support component 14 can have one of the two rectangular surfaces with the largest area make contact with the back of the user's head. In some cases, head support component 14 can be concave in the center of a flat surface to accommodate the rounded shape of the back of a user's head.

A head support component of a neck pain relieving device provided herein can be designed to have dimensions appropriate to allow a head support component to support at least some of the weight of a user's head. For example, a head support component of a neck pain relieving device provided herein can be between about 15 cm and about 35 cm in length (e.g., between about 20 cm and about 35 cm in length, between about 25 cm and about 35 cm in length, between about 30 cm and about 35 cm in length, between about 15 cm and about 30 cm in length, between about 15 cm and about 25 cm in length, or between about 20 cm and about 30 cm in length) and between about 5 cm and about 20 cm in width (e.g., between about 7 cm and about 20 cm in width, between about 10 cm and about 20 cm in width, between about 5 cm and about 15 cm in width, between about 5 cm and about 10 cm in width, between about 7 cm and about 10 cm in width, or between about 8 cm and about 10 cm in width) such that adequate contact between the head support component and the back of a user's head is made to support at least some of the weight of the user's head. Neck pain relieving devices can be made with different size head support components to support different head sizes.

A head support component of a neck pain relieving device provided herein can be composed of any appropriate material. For example, a head support component of a neck pain relieving device provided herein can be composed of a rigid material such that the head support component can support at least some of the weight of a user's head. Examples of rigid materials that can be used to make a head support component provided herein include, without limitation, stainless steel, aluminum, hard plastic, and wood.

Figure 4:
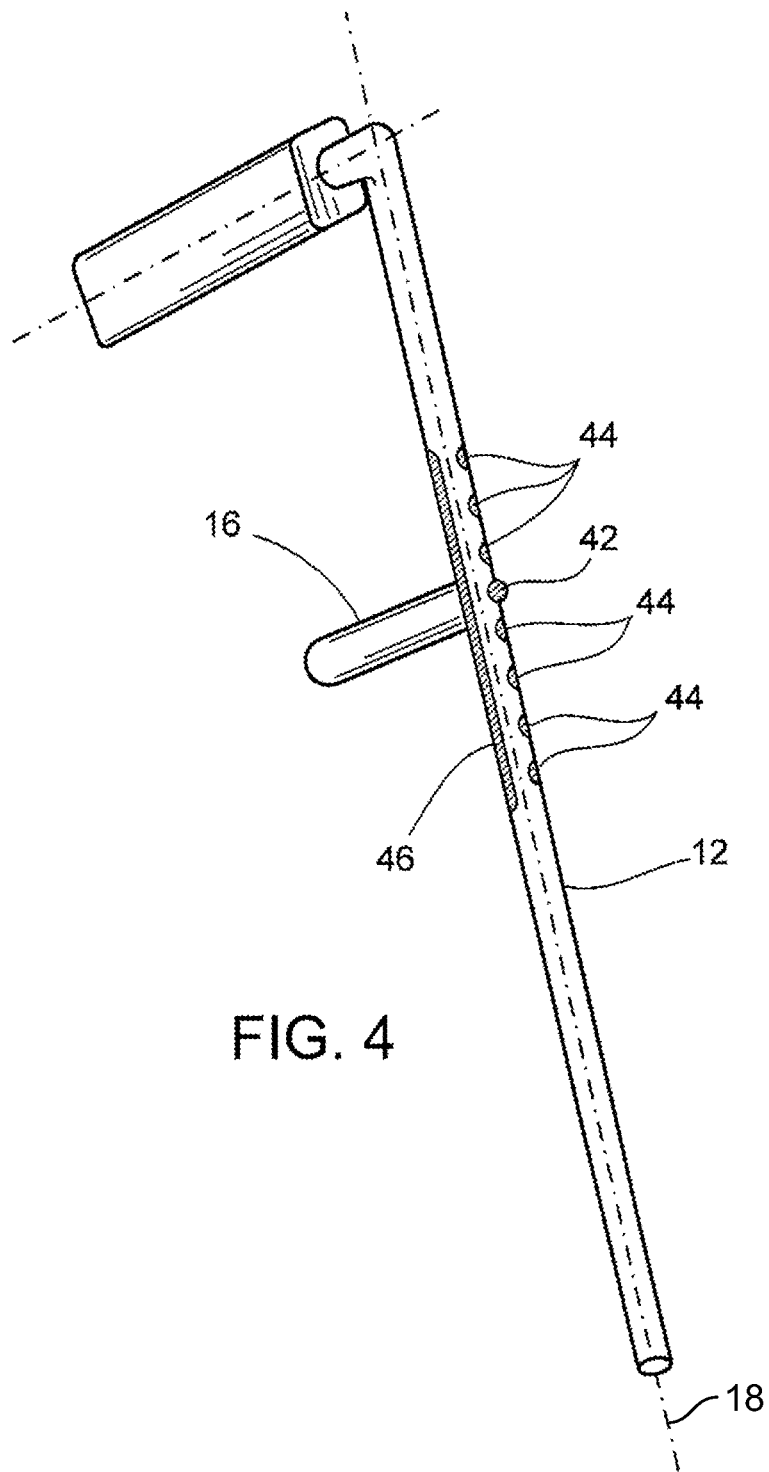
FIG. 4 a perspective view of an exemplary chest pivot component and portion of a rod provided herein.

A chest pivot component of a neck pain relieving device provided herein can be integral with or attached to a rod element and placed between the first and second ends of the rod element. With reference to FIG. 2, the placement of chest pivot component 16 should be such that when head support component 14 is behind a user's head, chest pivot component 16 rests on the user's upper chest. Chest pivot component 16 can be placed at different lengths below head support component 14 to fit different size users. In some cases, a portion of a rod element between a chest pivot component and a head support component can be telescopic to provide adjustable lengths. The length of a rod element can be adjusted to position a chest pivot component for different size users. In some cases, as shown in FIG. 4, chest pivot component 16 can be designed such that it is moveable along axis 18 of rod element 12 to accommodate users of different sizes. For example, chest pivot component 16 can have a depressible knob 42 on the opposite side rod element 12 from chest pivot component 16. Rod element 12 can be hollow and have holes 44 on the same side as depressible knob 42 in which depressible knob 42 can fit. Rod element 12 can have a cut-out track 46 along a portion of it's length on the same side as chest pivot component 16 such that chest pivot component 16 can slide along track 46 when depressible knob 42 is depressed. When chest pivot component 16 is at the desired location to fit a user properly, chest pivot component 16 can be locked in place by depressible knob 42 fitting through nearest hole 44 in rod element 12. In some cases, a similar arrangement can be configured to provide adjustment of the position of one or more head support components of a neck pain relieving device provided herein.

A chest pivot component of a neck pain relieving device provided herein can have any appropriate configuration that allows a chest pivot component to pivot on the upper chest of a user. For example, a chest pivot component can be cylindrical. With reference to FIG. 2, chest pivot component 16 can act as a fulcrum in the type I lever neck pain relieving device. With a cylindrical shape, chest pivot component 16 can pivot between a first end of a rod element and a head support component at a second end of the rod element.

A chest pivot component of a neck pain relieving device provided herein can be designed to have dimensions appropriate to allow a chest pivot component to pivot between a first end of a rod element and a head support component at a second end of the rod element. For example, a chest pivot component of a neck pain relieving device provided herein can be between about 10 cm and about 30 cm in length (e.g., between about 15 cm and about 30 cm in length, between about 18 cm and about 30 cm in length, between about 10 cm and about 25 cm in length, between about 10 cm and about 20 cm in length, between about 17 cm and about 23 cm in length, between about 17 cm and about 22 cm in length, between about 15 cm and about 22 cm in length, or between about 18 cm and about 22 cm in length) and between about 1 cm and about 8 cm in diameter (e.g., between about 2 cm and about 8 cm in diameter, between about 3 cm and about 5 cm in diameter, between about 1 cm and about 6 cm in diameter, between about 1 cm and about 5 cm in diameter, or between about 2 cm and about 4 cm in diameter).

A chest pivot component of a neck pain relieving device provided herein can be composed of any appropriate material. For example, a chest pivot component of a neck pain relieving device provided herein can be composed of a rigid material such that the chest pivot component can pivot between a first end of a rod element and a head support component at a second end of the rod element. Examples of rigid materials that can be used to make a chest pivot component provided herein include, without limitation, stainless steel, aluminum, hard plastic, and wood.

Figure 5:
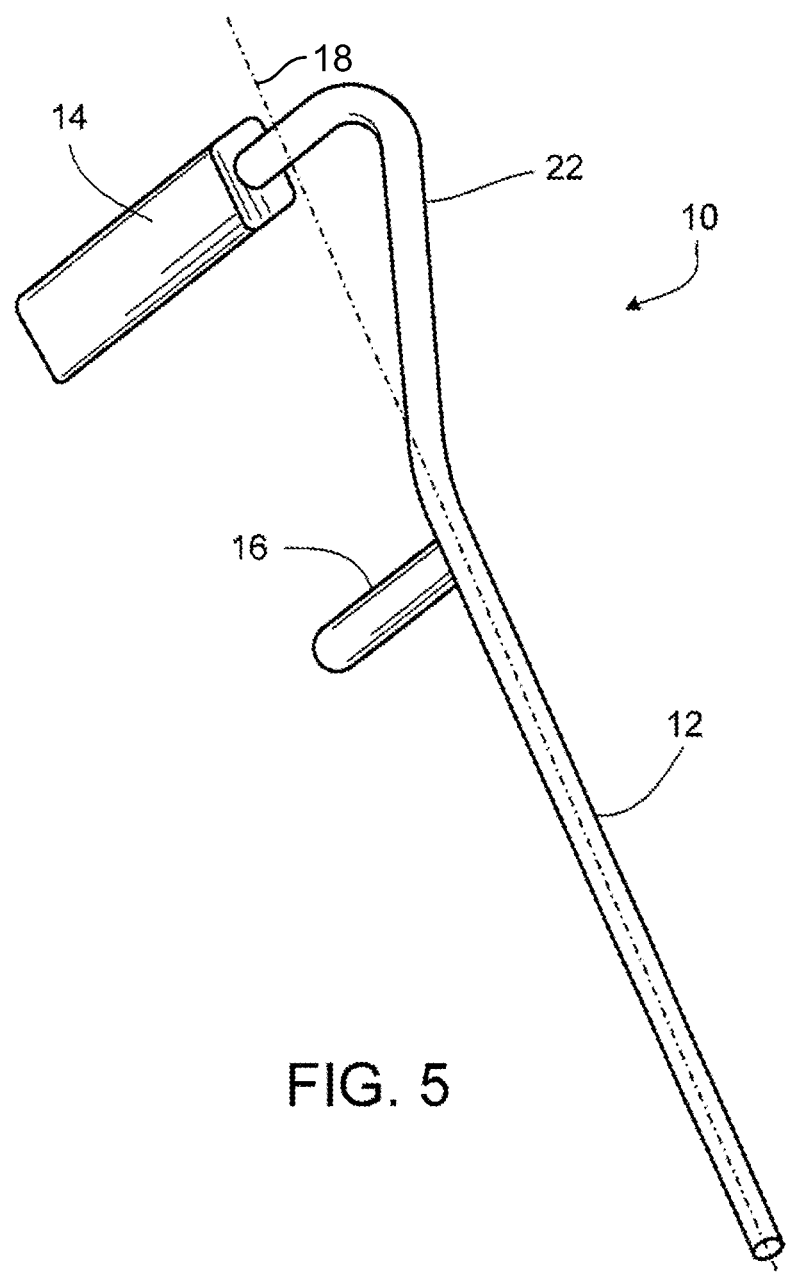
FIG. 5 is a perspective view of an exemplary neck pain relieving device provided herein.

A rod element of a neck pain relieving device provided herein can have any appropriate configuration that allows placement of one or more chest pivot components at the upper chest of a user and one or more head support components at the back of the user's head. For example, with reference to FIG. 5, rod element 12 of neck pain relieving device 10 can be curved. Second end 22 of rod element 12 can angle away from longitudinal axis 18 of rod element 12 by between about 1 to about 40 degrees (e.g., between about 5 to about 30 degrees, between about 10 to about 30 degrees, between about 15 to about 30 degrees, between about 1 to about 25 degrees, between about 1 to about 20 degrees, or between about 5 to about 25 degrees).

Second end 22 of rod element 12 can angle away from chest pivot component 16. Rod element 12 can terminate above the level of head support component 14 or rod element 12 can turn back towards vertical axis 18 at the level of head support component 14. Second end 22 of rod element 12 can be integral with head support component 14, or head support component 14 can fit over the end of rod element 12. In some cases, as shown in FIGS. 1 and 2, rod element 12 can be straight. In some cases, a rod element of a neck pain relieving device provided herein can be curved. In some cases, a rod element of a neck pain relieving device provided herein can be cylindrical. In some cases, a rod element of a neck pain relieving device provided herein can be configured to provide comfort having no edges pressing against a user during use.

A rod element of a neck pain relieving device provided herein can be designed to have dimensions appropriate to fit a user. Different length rod elements can be used in neck pain relieving devices to accommodate different size users. For example, a rod element of a neck pain relieving device provided herein can be between about 50 cm and about 100 cm in length (e.g., between about 60 cm and about 100 cm in length, between about 70 cm and about 100 cm in length, between about 75 cm and about 100 cm in length, between about 50 cm and about 95 cm in length, between about 50 cm and about 90 cm in length, between about 50 cm and about 85 cm in length, between about 50 cm and about 80 cm in length, or between about 60 cm and about 82 cm in length). With reference to FIG. 2, the length of rod element 12 can be such that head support component 14 contacts the back of a user's head and first end 20 of rod element 12 rests comfortably at about the position of a user's waist when seated. In some cases, a rod element can be telescopic to provide an adjustable length between a chest pivot component and a first end of the rod element. This can allow a user to adjust the length of a rod element such that it is comfortable for the user's size. A rod element of a neck pain relieving device provided herein can be between about 1 cm and about 10 cm in diameter (e.g., between about 2 cm and about 10 cm in diameter, between about 3 cm and about 10 cm in diameter, between about 1 cm and about 8 cm in diameter, between about 1 cm and about 6 cm in diameter, between about 2 cm and about 5 cm in diameter, or between about 2 cm and about 4 cm in diameter) such that the rod element has a large enough diameter to support a chest pivot component, a head support component, and the force applied at the first end of the rod element during use.

The first end of a rod element used in a neck pain relieving device provided herein can be configured for a user to hold the neck pain relieving device. For example, the first end of a rod element can have grooves or depressions such that a user can easily grip the first end of the rod element. The grooves or depressions can be made directly in the material of the rod element. In some cases, the first end of rod element can be covered with a non-slip material such that a user will not lose their grip on the first end of the rod element during use. The non-slip material can have a tactile surface. Examples of non-slip materials that can be used to cover the first end a rod element include, without limitation, rubber, PVC-coated fabric, polychloroprene, silicone, latex, and molded plastic.

A rod element of a neck pain relieving device provided herein can be composed of any appropriate material. For example, a rod element of a neck pain relieving device provided herein can be composed of a rigid material such that the rod element can support a chest pivot component, a head support component, and the force applied at the first end of the rod element during use. Examples of rigid materials that can be used to make a rod element provided herein include, without limitation, stainless steel, aluminum, hard plastic, and wood.

Any appropriate method can be used to make a neck pain relieving device provided herein. For example, common molding or casting techniques can be used to make an entire neck pain relieving device when one or more (e.g., two) head support components and one or more (e.g., two) chest pivot components are integral with the rod element. In some cases, common molding or casting techniques can be used to make a rod element, a head support component, and a chest pivot component when a head support component and a chest pivot component are attached to the rod element. Common attachment techniques can be used to attach one or more (e.g., two) head support components and one or more (e.g., two) chest pivot components to a rod element. In some cases, common manufacturing techniques can be used to make a cushion to cover a head support component and/or a chest pivot component of a neck pain relieving device provided herein. In some cases, common sewing techniques can be used to make a soft sleeve to cover a cushion covering a head support component and/or a chest pivot component of a neck pain relieving device provided herein.

Any appropriate method can be used to support the back of a user's head with a neck pain relieving device provided herein. For example, a neck pain relieving device provided herein can be positioned such that a head support component rests behind a user's head. A chest pivot component can rest on the upper chest of the user. The first end of a rod element can be at about the level of the user's waist. In this position, the rod element will extend from about the level of the user's waist to beyond the user's shoulder.

Once a head support component is positioned behind the user's head, force can be transferred to support the user's head. For example, the user can apply force at the first end of the rod element. The neck pain relieving device can function as a type I lever, such that a small amount of force applied at the first end of the rod element gains force at the second end of the rod element where a head support component pushes against the back of the user's head to support at least a portion of the weight of the user's head. The support of the head provided by a neck pain relieving device provided herein can relieve at least a portion of the load on the cervical spine and the cervical muscles, resulting in relief of neck pain.

Once a head support component is supporting the user's head, the amount of support provided to the head can be controlled by the user. For example, the more force a user applies to the first end of the rod element, the more supported the head will be. A user can lessen the amount of force applied at the first end of the rod element for less firm support of the head. Since a neck pain relieving device as described herein can function as a type I lever, the amount of applied force required from the user at the first end of the rod element is not large. The user can sit back and relax while applying force at the first end of the rod element as force is gained at a head support component.

As described herein, a neck pain relieving device can be used virtually anywhere. For example, a neck pain relieving device can provide head support and neck pain relief in public areas that have seating with little or no back and head support. A neck pain relieving device provided herein can have a size and shape that is not large or bulky. A neck pain relieving device provided herein can be used in public without disturbing or distracting others. Relaxing at home also can be improved with less neck pain by using a neck pain relieving device provided herein. Reclining in a chair, a bed, a sofa, or any other reclining position can be made more comfortable for those that suffer with neck pain due to the load on the cervical spine and muscles. In some cases, a neck pain relieving device provided herein can provide neck pain relief at home while sitting in any type of chair.

As described herein, a neck pain relieving device provided herein can be ambulatory. In some cases, a neck pain relieving device provided herein can be used as a cane to assist the user with standing or walking. For example, a head support component can be used as a handle, and the rod element can be used for stabilization while standing, stepping, walking, or climbing. In such cases, the tip of the first end of the rod element can have a textured rubber cap to prevent it from slipping on the ground or floor surface. In some cases, a head support component and a chest pivot component can have a hinge where they connect or attach to the rod element. The hinge can allow the head support component and the chest pivot component to fold flat along the axis of the rod element when not in use. In some cases, a neck pain relieving device provided herein can have a vertical configuration and can be used as a walking stick.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for relieving neck pain, wherein said device comprises:
   (a) a rod element having a first end region, a second end region, and a longitudinal axis extending from said first end region to said second end region,
   (b) a head support component having a proximal end, a distal end, and a longitudinal axis extending from said proximal end to said distal end, wherein said proximal end of said head support is attached to said second end region of said rod element, and wherein said longitudinal axis of said head support is perpendicular or substantially perpendicular to said longitudinal axis of said rod element, and
   (c) a chest pivot component having a proximal end, a distal end, and longitudinal axis extending from said proximal end of said chest pivot component to said distal end of said chest pivot component, wherein said proximal end of said chest pivot component is attached to said rod element at a position of said rod element located between said first end region and said second end region, wherein said longitudinal axis of said chest pivot component is perpendicular or substantially perpendicular to said longitudinal axis of said rod element, wherein said longitudinal axis of said head support component and said longitudinal axis of said chest pivot component are parallel or substantially parallel,
   wherein said head support component is positioned to contact the back of a head of a human user when said chest pivot component is positioned in contact with the upper chest of said human user,
   wherein said rod element at said second end region angles between about 5 and about 30 degrees from said longitudinal axis of said rod element, wherein said second end region of said rod element angles towards a line that is 180 degrees from said longitudinal axis of said chest pivot component.

2. The device of claim 1, wherein said head support component is covered by a cushion.

3. The device of claim 1, wherein said chest pivot component is covered by a cushion.

4. The device of claim 1, wherein said head support component is configured to support at least a portion of the weight of said head.

5. The device of claim 1, wherein said head support component is rectangular.

6. The device of claim 1, wherein said head support component comprises material selected from the group consisting of stainless steel, aluminum, hard plastic, wood, and combinations thereof.

7. The device of claim 1, wherein said rod element between said chest pivot component and said head support component is configured to be telescoping to adjust the length of said rod element.

8. The device of claim 1, wherein said chest pivot component is moveable along said longitudinal axis of said rod element.

9. The device of claim 1, wherein said chest pivot component is configured to pivot between said first end region and said second end region of said rod element.

10. The device of claim 1, wherein said chest pivot component comprises material selected from the group consisting of stainless steel, aluminum, hard plastic, wood, and combinations thereof.

11. The device of claim 1, wherein said second end region of said rod element turns towards said longitudinal axis of said rod element at the level of said head support component.

12. The device of claim 1, wherein said head support component is configured to fit over an end of said second end region of said rod element.

13. The device of claim 1, wherein said rod element is cylindrical.

14. The device of claim 1, wherein said rod element is configured to fit users of various sizes.

15. The device of claim 1, wherein said rod element comprises material selected from the group consisting of stainless steel, aluminum, hard plastic, wood, and combinations thereof.

16. A device for relieving neck pain, wherein said device comprises:
(a) a rod element having a first end region, a second end region, and a longitudinal axis extending from said first end region to said second end region,
(b) a head support component having a proximal end, a distal end, and a longitudinal axis extending from said proximal end to said distal end, wherein said proximal end of said head support is attached to said second end region of said rod element, and wherein said longitudinal axis of said head support is perpendicular or substantially perpendicular to said longitudinal axis of said rod element, and
(c) a chest pivot component having a proximal end, a distal end, and longitudinal axis extending from said proximal end of said chest pivot component to said distal end of said chest pivot component, wherein said proximal end of said chest pivot component is attached to said rod element at a position of said rod element located between said first end region and said second end region, wherein said longitudinal axis of said chest pivot component is perpendicular or substantially perpendicular to said longitudinal axis of said rod element, wherein said longitudinal axis of said head support component and said longitudinal axis of said chest pivot component are parallel or substantially parallel,
wherein said head support component is positioned to contact the back of a head of a human user when said chest pivot component is positioned in contact with the upper chest of said human user,
wherein said rod element between said first end region of said rod element and said chest pivot component is telescoping to have an adjustable length.

17. The device of claim 16, wherein said head support component is covered by a cushion.

18. A device for relieving neck pain, wherein said device comprises:
(a) a rod element having a first end region, a second end region, and a longitudinal axis extending from said first end region to said second end region,
(b) a head support component having a proximal end, a distal end, and a longitudinal axis extending from said proximal end to said distal end, wherein said proximal end of said head support is attached to said second end region of said rod element, and wherein said longitudinal axis of said head support is perpendicular or substantially perpendicular to said longitudinal axis of said rod element, and
(c) a chest pivot component having a proximal end, a distal end, and longitudinal axis extending from said proximal end of said chest pivot component to said distal end of said chest pivot component, wherein said proximal end of said chest pivot component is attached to said rod element at a position of said rod element located between said first end region and said second end region, wherein said longitudinal axis of said chest pivot component is perpendicular or substantially perpendicular to said longitudinal axis of said rod element, wherein said longitudinal axis of said head support component and said longitudinal axis of said chest pivot component are parallel or substantially parallel,
wherein said head support component is positioned to contact the back of a head of a human user when said chest pivot component is positioned in contact with the upper chest of said human user,
wherein said head support component and said chest pivot component are attached to said rod element with a hinge such that said head support component and said chest pivot component fold flat along the length of said rod element.

19. The device of claim 18, wherein said head support component is covered by a cushion.

20. A method of facilitating balance of a human user, wherein said method comprises placing weight of said human user on a device to support balance of said human user while said human user is standing, stepping, walking, or climbing, wherein said device comprises:
(a) a rod element having a first end region, a second end region, and a longitudinal axis extending from said first end region to said second end region,
(b) a head support component having a proximal end, a distal end, and a longitudinal axis extending from said proximal end to said distal end, wherein said proximal end of said head support is attached to said second end region of said rod element, and wherein said longitudinal axis of said head support is perpendicular or substantially perpendicular to said longitudinal axis of said rod element, and
(c) a chest pivot component having a proximal end, a distal end, and a longitudinal axis extending from said proximal end of said chest pivot component to said distal end of said chest pivot component, wherein said proximal end of said chest pivot component is attached to said rod element at a position of said rod element located between said first end region and said second end region, wherein said longitudinal axis of said chest pivot component is perpendicular or substantially perpendicular to said longitudinal axis of said rod element, wherein said longitudinal axis of said head support component and said longitudinal axis of said chest pivot component are parallel or substantially parallel,
wherein said head support component is positioned to contact the back of a head of said human user when said chest pivot component is positioned in contact with the upper chest of said human user.

* * * * *